US012567141B2

(12) United States Patent
Zhang et al.

(10) Patent No.:  US 12,567,141 B2
(45) Date of Patent:       Mar. 3, 2026

(54) MEDICAL IMAGE SYNTHESIS DEVICE AND METHOD

(71) Applicant: GE Precision Healthcare LLC, Wauwatosa, WI (US)

(72) Inventors: Chen Zhang, Guangzhou (CN); Yanmei Wang, Beijing (CN); Jingjing Xia, Shanghai (CN); Linshang Rao, Guangzhou (CN); Zhoushe Zhao, Beijing (CN); Zhijie Huang, Guangzhou (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 710 days.

(21) Appl. No.: 17/840,184

(22) Filed: Jun. 14, 2022

(65) Prior Publication Data

US 2022/0414874 A1      Dec. 29, 2022

(30) Foreign Application Priority Data

Jun. 23, 2021    (CN) .......................... 202110700593.2

(51) Int. Cl.
        *G06T 7/00*           (2017.01)
        *A61B 6/03*           (2006.01)
(52) U.S. Cl.
        CPC ............ *G06T 7/0012* (2013.01); *A61B 6/032* (2013.01); *G06T 2207/10081* (2013.01); *G06T 2207/30004* (2013.01)
(58) Field of Classification Search
        CPC ......... G06T 7/0012; G06T 2207/10081; G06T 2207/30004; G06T 5/94; G06T 2207/10088; G06T 2207/10104; G06T 2207/20221; G06T 5/50; G06T 2207/10024; G06T 2207/20081; G06T 2207/20084; A61B 6/032; A61B 6/5235; G16H 30/20
        See application file for complete search history.

(56) References Cited

U.S. PATENT DOCUMENTS

| | | | | |
|---|---|---|---|---|
| 11,080,897 | B2 * | 8/2021 | Li | ........................ G06T 11/008 |
| 11,164,345 | B2 * | 11/2021 | Feng | ....................... G06T 7/337 |
| 2010/0054571 | A1 * | 3/2010 | Kojima | ............... G01N 23/046 |
| | | | | 382/131 |

(Continued)

FOREIGN PATENT DOCUMENTS

| | | | | |
|---|---|---|---|---|
| CN | 109272476 | A | 1/2019 | |
| CN | 111312373 | A * | 6/2020 | ............... G06T 7/66 |

*Primary Examiner* — Oneal R Mistry
*Assistant Examiner* — Jongbong Nah

(57)                    ABSTRACT

Embodiments of the present application provide a medical image synthesis device and method. According to an embodiment, a method includes acquiring a first medical image and a second medical image and registering the first medical image with the second medical image. The method includes determining a first parameter value at each pixel location on the registered first medical image and a second parameter value at each pixel location on the second medical image. The method includes multiplying the first parameter value with the second parameter value at the same pixel location on the registered first medical image and the second medical image and generating synthetic image data based on the multiplication result.

19 Claims, 5 Drawing Sheets

(56)        References Cited

U.S. PATENT DOCUMENTS

| 2012/0019548 | A1* | 1/2012 | Zhu | ....................... | G06T 11/001 |
| | | | | | 345/589 |
| 2016/0217585 | A1* | 7/2016 | Yoshida | ................ | G06T 7/0012 |
| 2018/0374205 | A1* | 12/2018 | Zhu | ....................... | G06T 11/008 |
| 2019/0266709 | A1* | 8/2019 | Takeda | ................... | H04N 1/393 |
| 2020/0126231 | A1* | 4/2020 | Hu | ....................... | G06T 11/005 |
| 2020/0327672 | A1* | 10/2020 | Yao | ....................... | A61B 6/032 |
| 2020/0342600 | A1* | 10/2020 | Sjöstrand | ............. | A61B 6/5229 |

* cited by examiner

101

Acquire a first medical image and a
second medical image

102

Register the first medical image with the
second medical image

103

Determine a first parameter value at each pixel
location on the registered first medical image and
a second parameter value at each pixel location
on the second medical image

104

Multiply the first parameter value and the second parameter
value at the same pixel location on the registered first
medical image and the second medical image, and generate
synthetic image data based on the multiplication result

FIG. 1

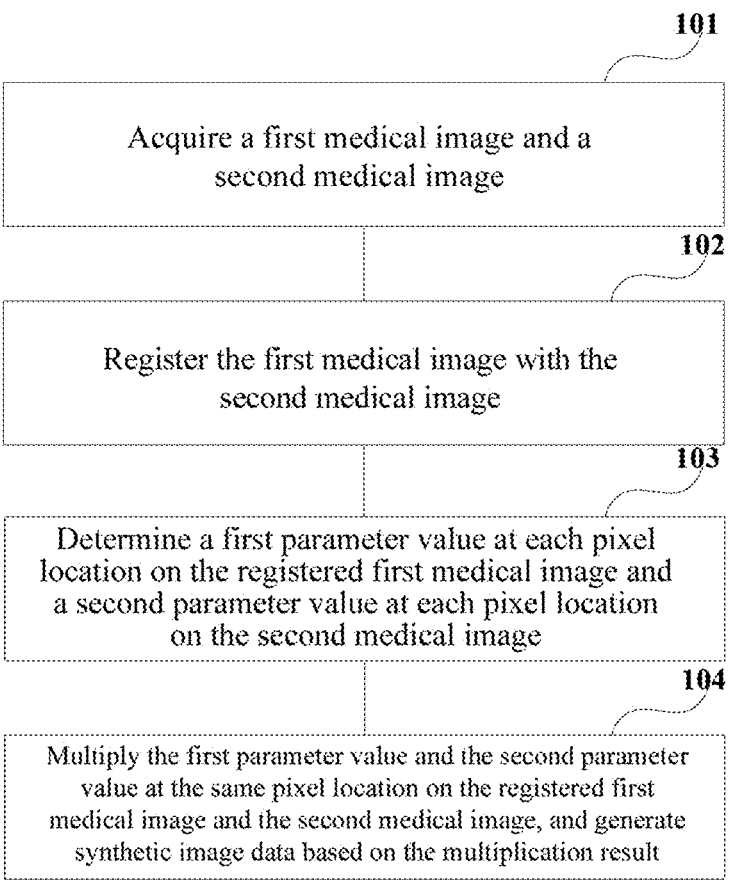

$$
\begin{bmatrix} a_{11} & a_{12} & \ldots & a_{1H} \\ a_{21} & a_{22} & \ldots & a_{2H} \\ \ldots & \ldots & \ldots & \ldots \\ a_{W1} & a_{W2} & \ldots & a_{WH} \end{bmatrix} \times \begin{bmatrix} b_{11} & b_{12} & \ldots & b_{1H} \\ b_{21} & b_{22} & \ldots & b_{2H} \\ \ldots & \ldots & \ldots & \ldots \\ b_{W1} & b_{W2} & \ldots & b_{WH} \end{bmatrix} = \begin{bmatrix} a_{11} \times b_{11} & a_{12} \times b_{12} & \ldots & a_{1H} \times b_{1H} \\ a_{21} \times b_{21} & a_{22} \times b_{22} & \ldots & a_{2H} \times b_{2H} \\ \ldots & \ldots & \ldots & \ldots \\ a_{W1} \times b_{W1} & a_{W2} \times b_{W1} & \ldots & a_{WH} \times b_{WH} \end{bmatrix}
$$

MEDICAL IMAGE SYNTHESIS DEVICE AND METHOD

CROSS-REFERENCE TO RELATED APPLICATION

This application claims priority to Chinese patent application number 202110700593.2, filed on Jun. 23, 2021, the entirety of which is incorporated herein by reference.

TECHNICAL FIELD

Embodiments of the present application relate to the technical field of medical apparatuses, in particular to a medical image synthesis device and method.

BACKGROUND

At present, medical imaging apparatuses are being used more and more widely to scan subjects (e.g., a human body) to obtain medical images of specified regions (e.g., the whole or parts of various organs in the human body, or specific regions of interest) to provide useful information for medical diagnosis. Medical image scanning includes Computed Tomography (CT), Magnetic Resonance Imaging (MRI), Positron Emission Tomography (PET) and Single Photon Emission Computed Tomography (SPECT), etc. Wherein, since different tissues or organs have different attenuation coefficients or absorption coefficients for X-rays, CT images are cross-sectional tomographic images of the human body, which can reflect the anatomical structure of the human body. PET or SPECT images selectively reflect the metabolism, receptor and gene expressions of target tissue cells according to a radioactive tracer, which can reflect the physiological, pathological, biochemical and metabolic changes of human tissues at a molecular level at an early stage, while the PET/CT image and SPECT/CT image are an imaging modality that combines functional metabolic molecular imaging and anatomical structure imaging together. PET/CT has unique value in the diagnosis of diseases such as oncological diseases, cardiovascular and cerebrovascular diseases, neurodegenerative diseases and epilepsy. SPECT/CT imaging, on the other hand, is widely used for the diagnosis of a variety of clinical diseases such as bone, heart diseases and tumor. MRI can reflect tissue structures and metabolism through changes in tissue cell T1 and T2 values and proton distribution densities.

Among the methods in the prior art, those that can achieve fusion of PET images or SPECT images with CT images mainly include: conventional superposition fusion methods and deep learning-based methods. Wherein, the conventional superposition fusion method is to adjust the CT image to a certain transparency and then superimpose the PET or SPECT image directly onto the CT image to form a fusion image. However, the inventors found that the fusion image obtained by this method cannot accurately identify the lesion. For example, the low contrast of the fusion image makes it impossible to accurately identify the lesion, or in some cases small lesions in the cavity organs (such as the renal pelvis, blood vessel wall and intestine, etc.) where tracers are distributed cannot be accurately identified.

Alternatively, a deep learning-based method is to input PET or SPECT images and CT images into a trained convolutional neural network model and the output of such a model is a PET/CT image or a SPECT/CT image. However, the inventors found the following problems with the deep learning-based methods: since the fused image is of the same nature as the source images, it has limited effect on the improvement of image resolution and contrast. In addition, deep learning-based methods are highly dependent on training data, and the insufficient amount of training data will affect the performance of deep learning networks, which in turn affects the image fusion effect. Furthermore, the resolution of the fused images is still relatively low, and the effectiveness of detecting some small lesions and cavity organ lesions is relatively poor. Since the standardized uptake values of images of normal tissues such as the kidney, ureter and bladder are too high, some small lesions can be obscured, leading to missed diagnosis or misdiagnosis, thus reducing the accuracy of diagnosis.

Embodiments of the present application provide a medical image synthesis device and method that can increase tissue density information while further improving image resolution and contrast, thereby enabling clear display of lesions and improving lesion detection effectiveness.

BRIEF DESCRIPTION

According to an embodiment, a medical image synthesis device includes an acquisition unit used to acquire a first medical image and a second medical image. The medical image synthesis device includes a registration unit used to register said first medical image with said second medical image. The medical image synthesis device includes a determination unit used to determine a first parameter value at each pixel location on the registered first medical image and a second parameter value at each pixel location on the second medical image. The medical image synthesis device includes a generation unit used to multiply the first parameter value with the second parameter value at the same pixel location on the registered first medical image and the second medical image, and generate synthetic image data based on the multiplication result.

According to an embodiment, a method used for synthesizing a medical image includes acquiring a first medical image and a second medical image and registering said first medical image with said second medical image. The method includes determining a first parameter value at each pixel location on the registered first medical image and a second parameter value at each pixel location on the second medical image. The method includes multiplying the first parameter value with the second parameter value at the same pixel location on the registered first medical image and the second medical image, and generating synthetic image data based on the multiplication result.

According to an embodiment, a storage medium having a computer-readable program stored thereon causes a computer to perform the following steps. Acquiring a first medical image and a second medical image. Registering said first medical image with said second medical image. Determining a first parameter value at each pixel location on the registered first medical image and a second parameter value at each pixel location on the second medical image. Multiplying the first parameter value with the second parameter value at the same pixel location on the registered first medical image and the second medical image, and generating synthetic image data based on the multiplication result.

With reference to the following description and accompanying drawings, specific implementations of the embodiments of the present application are disclosed in detail, and manners in which the principle of the embodiments of the present application is employed are illustrated. It should be understood that the implementations of the present application are not thereby limited in scope. Within the spirit and scope of the appended claims, the implementations of the present application comprise various changes, modifications, and equivalents.

BRIEF DESCRIPTION OF THE DRAWINGS

The accompanying drawings are included to provide further understanding of embodiments of the present application, constitute a part of the specification, and are used to illustrate implementations of the present application and set forth the principles of the present application together with textual description. Obviously, the accompanying drawings in the following description are merely some embodiments of the present application, and a person of ordinary skill in the art could obtain other implementations according to the accompanying drawings without the exercise of inventive effort. In the accompanying drawings:

FIG. 1 is a schematic diagram of a medical image synthesis method of an embodiment of the present application.

FIG. 2 is a schematic diagram of a matrix dot-multiplication of an embodiment of the present application.

DETAILED DESCRIPTION

Figure 3:
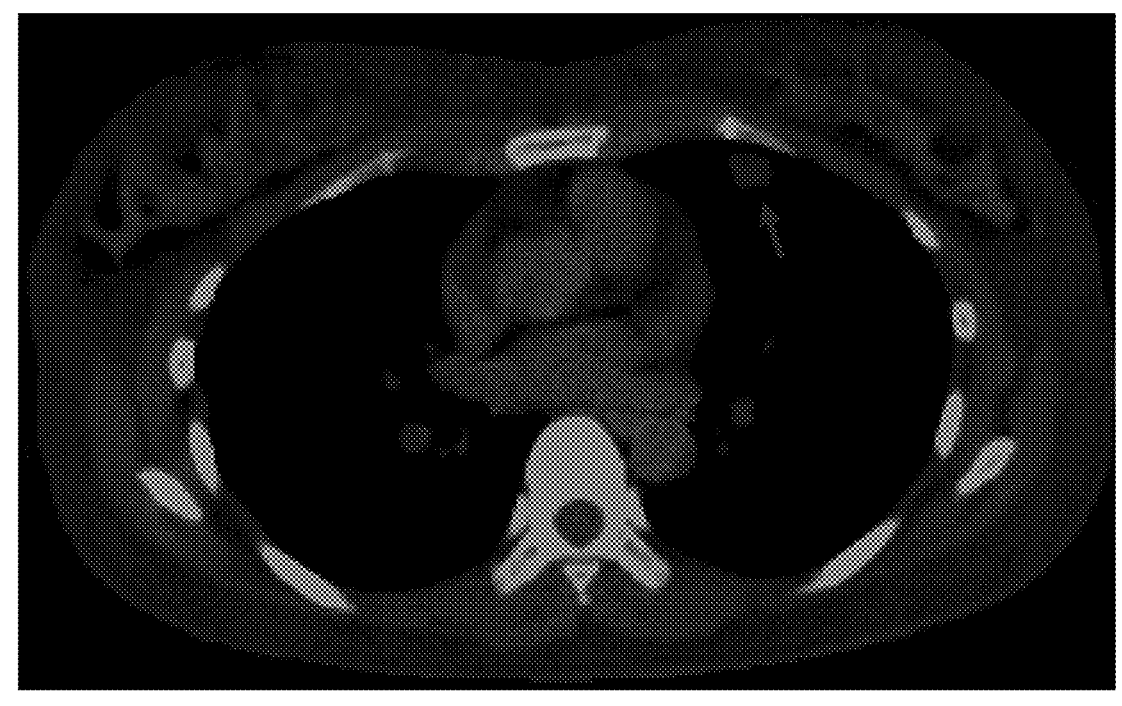
FIG. 3 is a schematic diagram of a grayscale synthetic image of an embodiment of the present application.

The foregoing and other features of the embodiments of the present application will become apparent from the following description with reference to the accompanying drawings. In the description and the accompanying drawings, specific implementations of the present application are specifically disclosed, and part of the implementations in which the principles of the embodiments of the present application may be employed are indicated. It should be understood that the present application is not limited to the described implementations. On the contrary, the embodiments of the present application include all modifications, variations, and equivalents falling within the scope of the appended claims.

In the embodiments of the present application, the terms "first," "second," etc. are used to distinguish different elements, but do not represent a spatial arrangement or temporal order etc. of these elements, and these elements should not be limited by these terms. The term "and/or" includes any one of and all combinations of one or more associated listed terms. The terms "comprise," "include," "have," etc. refer to the presence of described features, elements, components, or assemblies, but do not exclude the presence or addition of one or more other features, elements, components, or assemblies.

In the embodiments of the present application, the singular forms "a," "the," etc. include plural forms, and should be broadly construed as "a type of" or "a class of" rather than limited to the meaning of "one." Furthermore, the term "said" should be construed as including both the singular and plural forms, unless otherwise specified in the context. In addition, the term "according to" should be construed as "at least in part according to . . . ," and the term "based on" should be construed as "at least in part based on . . . ," unless otherwise specified in the context.

The features described and/or illustrated for one implementation may be used in one or more other implementations in the same or similar manner, combined with features in other implementations, or replace features in other implementations. The term "include/comprise" when used herein refers to the presence of features, integrated components, steps, or assemblies, but does not preclude the presence or addition of one or more other features, integrated components, steps, or assemblies.

The apparatus described herein for obtaining medical imaging data may be suitable for a variety of medical imaging modalities, including but not limited to Computed Tomography (CT) apparatuses, Magnetic Resonance Imaging (MRI) apparatuses, Positron Emission Tomography (PET) apparatuses, Single Photon Emission Computed Tomography (SPECT) apparatuses, PET/CT, PET/MRI, or any other appropriate medical imaging apparatuses.

The medical imaging system may include the aforementioned medical imaging apparatus, and may include a separate computer apparatus connected to the medical imaging apparatus, and may further include a computer apparatus connected to an Internet cloud, which is connected via the Internet to the medical imaging apparatus or a memory for storing medical images. The imaging method may be independently or jointly implemented by the aforementioned medical imaging apparatus, the computer apparatus connected to the medical imaging apparatus, and the computer apparatus connected to the Internet cloud.

For example, the CT scan uses X-rays to carry out continuous profile scans around a part of the scanned object, and the detectors receive the X-rays that pass through that plane and transforms them into visible light or convert the received photon signal directly and then reconstructs the image through a series of processes. MRI is based on the principle of nuclear magnetic resonance of atomic nuclei, and forms an image through reconstruction by transmitting radio frequency pulses to the scanned object and receiving electromagnetic signals emitted from the scanned object.

PET scan uses a cyclotron to accelerate charged particles to bombard a target nucleus, which produces positron-bearing radionuclides through nuclear reactions and synthesizes imaging agents that are introduced into the body and localized in the target organ. They emit positrons during the decay process, and after the positron travels a short distance in the tissue, it interacts with the electrons in the surrounding material and annihilation radiation occurs, emitting two photons of opposite directions and equal energy. PET imaging uses a series of paired detectors that are registered 180 degrees to each other and receive coincidence lines to detect the photons of annihilating radiation produced by the tracer outside the body, and the collected information is processed by a computer to obtain a reconstructed image.

SPECT uses a radioactive isotope as a tracer, and this tracer is injected into the human body so that the tracer is concentrated on the organ to be examined, thus making the organ a source of y-rays, and the distribution of radioactivity in organ tissues is recorded outside the body using detectors that rotate around the human body. One set of data is obtained when the detectors rotate to one angle and several sets of data can be obtained when the detectors rotate for a full circle. From this data a series of tomographic planar images can be created and the computer reconstructs the imaging in a cross-sectional manner.

PET and SPECT extend a histopathological examination of local tissues from a molecular level to a biochemistry display, and the images provided are images of human physiological metabolism, which are distinguished by functional imaging and can detect functional and metabolic changes in the process of disease occurrence and development, while CT and MRI are distinguished by their ability to accurately reflect morphological and structural changes. With methods in the prior art, CT or MRI may be used for attenuation correction of PET or SPECT images. That is, PET or SPECT and CT or MRI images are fused into one so that the functional and anatomical image information can be complementary to each other to achieve better identification and diagnosis.

In addition, the medical imaging workstation may be disposed locally to the medical imaging apparatus. That is, the medical imaging workstation is disposed adjacent to the medical imaging apparatus, and the medical imaging workstation and medical imaging apparatus may be located together in a scanning room, an imaging department, or in the same hospital. The medical image cloud platform analysis system may be located away from the medical imaging apparatus, for example, arranged at a cloud end that is in communication with the medical imaging apparatus.

As an example, after a medical institution completes an imaging scan using the medical imaging apparatus, scan data is stored in the storage apparatus. The medical imaging workstation may directly read the scan data and perform image processing by means of a processor thereof. As another example, the medical image cloud platform analysis system may read a medical image in the storage apparatus by means of remote communication to provide "software as a service (SAAS)." SAAS can exist between hospitals, between a hospital and an imaging center, or between a hospital and a third-party online diagnosis and treatment service provider.

FIG. 1 is a schematic diagram of a medical image synthesis method of an embodiment of the present application. FIG. 1 includes a step 101, a step 102, a step 103, and a step 104. Step 101 includes acquiring a first medical image and a second medical image. Step 102 includes registering the first medical image with the second medical image. Step 103 includes determining a first parameter value at each pixel location on the registered first medical image and a second parameter value at each pixel location on the second medical image. Step 104 includes multiplying the first parameter value and the second parameter value at the same pixel location on the registered first medical image and the second medical image. Step 104 also includes generating synthetic image data based on the multiplication result.

It should be noted that FIG. 1 merely schematically illustrates the embodiment of the present application, but the present application is not limited thereto. For example, the order of execution between operations may be suitably adjusted. In addition, some other operations may also be added or some of these operations may be omitted. Those skilled in the art could make appropriate variations according to the above disclosure, rather than being limited by the disclosure of FIG. 1.

In some embodiments, said first medical image and second medical image are images corresponding to the same scanned object or the region of interest of the same scanned object, and said first medical image and second medical image are medical images obtained based on different imaging principles. For example, the first medical image is an anatomical image, which can provide precise anatomical positioning of tissues or organs, including CT images or MRI images, etc.; while the second medical image is a molecular image, which can provide information on the function or metabolism of the tissues or organs, including PET images or SPECT images, etc. The embodiments of the present application are not limited thereto, which will not be exemplified one by one herein.

In some embodiments, in 101, the first medical image and the second medical image data are acquired to obtain image data of the first medical image and image data of the second medical image. The data type of the image data may be a DICOM file or an NIFTI file, and the image data (or data file) may include the following information: pixel depth, luminosity interpretation (indicating whether the image is displayed as a monochrome image or color image, for example, the first medical image is usually a monochrome image and the second medical image is usually a color image, but the embodiments of the present application are not limited thereto), metadata (including image matrix dimensionality and spatial accuracy, etc.), pixel data (the size of the pixel values at each location, expressed using integer or floating point data types), and with respect to the specific format of the above DICOM file or NIFTI file, the prior art may be referred to, which will not be repeated herein. For example, the above pixel data may be represented using a matrix whose rows correspond to the height of the image (in pixels), whose columns correspond to the width of the image (in pixels), whose individual elements correspond to the pixels at the corresponding locations in the image, and the element values are the pixel values (grayscale values).

In some embodiments, in 102, the first medical image is registered with the second medical image. For example, the second medical image may be matched to the first medical image by a rigid registration method of mutual information. For example, the mutual information of the first medical image and the second medical image is calculated and the mutual information is continuously calculated after various translations and rotations of the second medical image, and the second medical image is matched to the first medical image when the mutual information is maximized. Meanwhile, the rotation matrix and translation vectors are obtained when the second medical image is registered and the second medical image is processed by the rotation matrix and translation vectors to achieve the registration of the first medical image with the second medical image. The above is only an illustration, and embodiments of the present application are not limited thereto, and other registration methods may be used for registration. In addition, the first medical image may also be matched to the second medical image, which is not exemplified one by one herein.

In some embodiments, in order to improve the image resolution, and the image fusion results, the first medical image and the second medical image may also be preprocessed before image fusion is performed, i.e., the method may also include: carrying out at least one of re-sampling, image enhancement, and image denoising preprocessing procedures on the first medical image and the second medical image.

For example, re-sampling of the first medical image and the registered second medical image (or re-sampling of the second medical image and the registered first medical image) may be based on the nearest-neighbor interpolation method by taking the pixel value at the relative location of the source image as the pixel value of the target image based on the ratio (scaling ratio) of the width (or height) of the target image to the width (or height) of the source image. For example, the scaling ratio in each direction may be set as follows: x-spacing=1; y-spacing=1; z-spacing=2. The above is only an example illustration, but embodiments of the present application are not limited thereto. For example, linear interpolation and other methods may also be used. Specific reference can be made to the prior art, which will not be repeated herein.

For example, image enhancement of the first medical image and the registered second medical image (or image enhancement of the second medical image and the registered first medical image) may be performed using Laplace's method, but embodiments of the present application are not limited thereto. For example, other methods such as histogram averaging may also be used. Specific reference can be made to the prior art, which will not be repeated herein.

For example, image denoising of the first medical image and the registered second medical image (or image denoising of the second medical image and the registered first medical image) may be performed using Gaussian blurring. For example, the Gaussian blurring parameters (Gaussian blurring radius) of the first medical image and the second medical image may be set separately, but embodiments of the present application are not limited thereto. For example, other methods such as median filtering may also be used. Specific reference can be made to the prior art, which will not be repeated herein.

It should be noted that the present embodiment is not limited to the order of execution of the preprocessing steps such as re-sampling, image enhancement, and image denoising. Some other preprocessing operations may also be added. A person skilled in the art may implement appropriate variations based on the above disclosure, and the embodiments of the present application are not limited thereto.

In some embodiments, in 103, a first parameter value at each pixel location on the registered first medical image and a second parameter value at each pixel location on the second medical image are determined. For example, where the first medical image is a CT image and the second medical image is a PET or SPECT image, the first parameter value is a value corresponding to a linear attenuation coefficient of tissues or organs to rays of radiation, i.e., the CT value (in HU), which measures the absorption rate of radiation by the tissue or organ, and the second parameter value is a standardized uptake value (SUV, in g/mL), which is the ratio of the measured specific activity to the dose administered per body weight in the region of interest, which may be used to evaluate the benignity or malignancy of the lesion. The following explains how to determine the first parameter value and the second parameter value, respectively.

In some embodiments, the first parameter value may be determined based on the first pixel value (grayscale value) at each pixel location on the first medical image. For example, if the image data of the first medical image is stored in the form of a DICOM file, the first pixel value may be multiplied by the slope then added to the intercept to obtain the first parameter value, and the slope and the intercept are also included in the tag of the DICOM file. When the weighting coefficient is 1 and the predetermined value is 0, then the first pixel value is equal to the first parameter value. If the image data of the first medical image is stored in the form of an NIFTI file, the first pixel value may be multiplied and converted to the first parameter value using a predetermined function, and for the predetermined function, the prior art may be referred to, which will not be described one by one herein.

As shown in Table 1 below, the first parameter value of water is usually 0, the first parameter value of air is usually −1000, the first parameter value of fat is usually less than 0, the first parameter value of the bladder is usually 0, the first parameter value of the intestine is usually 0 or −1000, and the first parameter value of parenchymal organs may be set to A (where A is not equal to 0), and for the value of A, the prior art may be referred to, which will not be exemplified one by one herein.

In some embodiments, the second parameter value may be determined according to the second pixel value of each pixel location on the registered second medical image. For example, if the image data of the second medical image is stored in the form of a DICOM file, the second pixel value may be multiplied by the slope then added to the intercept, and then the second parameter value may be calculated in conjunction with the injection scan time and the half-life of the nuclide (for the calculation formula, the prior art may be referred to, which will not be exemplified herein), and the slope and the intercept may also be included in the tag of the DICOM file. If the image data of the second medical image is stored in the form of an NIFTI file, in addition to calculating the second parameter value based on the second pixel value using methods in the prior art, it is also necessary to correct the second parameter value based on the information of the scanned object (e.g., the BW coefficient) to determine the corrected second parameter value, and the corrected second parameter value is used as the second parameter value at each pixel location on the second medical image.

As shown in Table 1 below, the second parameter value of water is usually greater than 0, the second parameter value of air is usually 0, the second parameter value of fat is usually greater than 0 or equal to 0, the second parameter value of the bladder is usually greater than 0, the second parameter value of the intestine is usually 0, and the second parameter value of parenchymal organs may be set to B (where B is not equal to 0), and for the value of B, the prior art may be referred to, which will not be exemplified one by one herein.

In some embodiments, in 104, the first parameter value and the second parameter value at the same pixel location are multiplied. For example, the width and height of the registered and preprocessed first medical image and second medical image are W and H respectively (where W and H are positive integers), i.e., including W×H pixel locations. For example, each pixel location may be numbered in the order of first the row and then the column, and the aforementioned same pixel location refers to the pixel location with the same number. For the convenience of description below, the product of the first parameter value and the second parameter value at the same pixel location is referred to as the third parameter value (the unit is, for example, HU·g/mL). As shown in Table 1 below, the third parameter value of water is 0, the third parameter value of air is 0, the third parameter value of fat is usually less than 0 or is equal to 0, the third parameter value of the bladder is 0, and the third parameter value of the intestine is usually less than 0 or equal to 0, and the third parameter value of parenchymal organs may be set as A×B (where A×B is not equal to 0), which will not be exemplified one by one herein.

In general, the SUV is higher for higher malignancy, and the SUV is usually taken clinically to identify malignant tumors and benign lesions, and to suggest the malignancy of the tumor. According to clinical experience, if the SUV is greater than 2.5, then it should be considered as a malignant tumor, and if it is between 2 and 2.5, then it is within the critical range, and if it is less than 2.0, then it can be considered as a benign lesion. Therefore, for the lesion regions, especially the small lesion regions, vascular wall and cavity organ lesions, the multiplication of the first parameter value with the second parameter value is equivalent to an amplification of the pixel values at the corresponding locations, thus increasing the contrast and resolution of the synthetic image and making the lesion region clearer, thereby improving the lesion detection effectiveness.

In addition, the meaning of the third parameter value is different from that of the second parameter value and the first parameter value. Therefore, the synthetic image is different in nature from the original image and can reflect tissue density information, in addition to the basic anatomical and metabolic information.

TABLE 1

| Name | First parameter value | Second parameter value | Third parameter value |
|---|---|---|---|
| Water | 0 | >0 | 0 |
| Air | −1000 | 0 | 0 |
| Fat | <0 | 0 or > 0 | 0 or < 0 |
| Bladder | 0 | >0 | 0 |
| Intestine | 0 or −1000 | 0 | 0 |
| Parenchyma organs | A | B | A × B |

In some embodiments, the first parameter value at each pixel location of the first medical image may be represented using a first image matrix, and the second parameter value at each pixel location of the second medical image may be represented using a second image matrix. In 104, multiplying the first parameter value with the second parameter value at the same pixel location is equivalent to dot-multiplying the first image matrix and the second image matrix, i.e., dot-multiplying the matrices. FIG. 2 is an example diagram of dot-multiplication of the matrices. As shown in FIG. 2, both the first image matrix and the second image matrix are W×H dimensional matrices, and the result of dot-multiplication, i.e., the third image matrix, is also a w×H dimensional matrix.

In some embodiments, the first parameter value and the second parameter value may multiplied directly, or the first parameter value and/or the second parameter value may be corrected using weighting coefficients and then multiplied, as illustrated by the following examples.

For example, the first parameter value is corrected using the first weighting coefficient (the first weighting coefficient multiplied by the first parameter value), and the second parameter value is corrected using the second weighting coefficient (the second weighting coefficient multiplied by the second parameter value), and the corrected first parameter value and the corrected second parameter value at the same pixel location are multiplied, or the first image matrix is multiplied with the first weighting coefficient, then second image matrix is multiplied with the second weighting coefficient, and then the corrected first image matrix and the corrected second image matrix are dot-multiplied.

For example, the first parameter value is corrected using the first weighting coefficient (the first weighting coefficient multiplied by the first parameter value), and the second parameter value is corrected using the second weighting coefficient (the second weighting coefficient multiplied by the second parameter value), and the corrected first parameter value and the corrected second parameter value at the same pixel location are multiplied, or the first image matrix is multiplied with the first weighting coefficient, then the second image matrix is multiplied with the second weighting coefficient, and then the corrected first image matrix and the corrected second image matrix are dot-multiplied.

For example, only the first parameter value is corrected using the first weighting coefficient (the first weighting coefficient multiplied by the first parameter value), and the corrected first parameter value and second parameter value at the same pixel location are multiplied, or the first image matrix is multiplied with the first weighting coefficient and then dot-multiplied with the second image matrix.

For example, only the second parameter value is corrected using the second weighting coefficient (the second weighting coefficient multiplied by the second parameter value), and the corrected second parameter value and first parameter value at the same pixel location are multiplied, or the second image matrix is multiplied with the second weighting coefficient and then dot-multiplied with the first image matrix.

The first weighting coefficient and the second weighting coefficient may be determined as required. As corrections are carried out with the above weighting coefficients, the multiplication can further amplify the pixel values at the corresponding locations, thus resulting in a synthetic image with higher contrast and resolution, and thereby making the lesion region clearer.

In some embodiments, the multiplication result may be used as the pixel value at the same pixel location corresponding to the synthetic image; or, a mapping value corresponding to the multiplication result may be determined as the pixel value at the same pixel location corresponding to the synthetic image.

Figure 4:
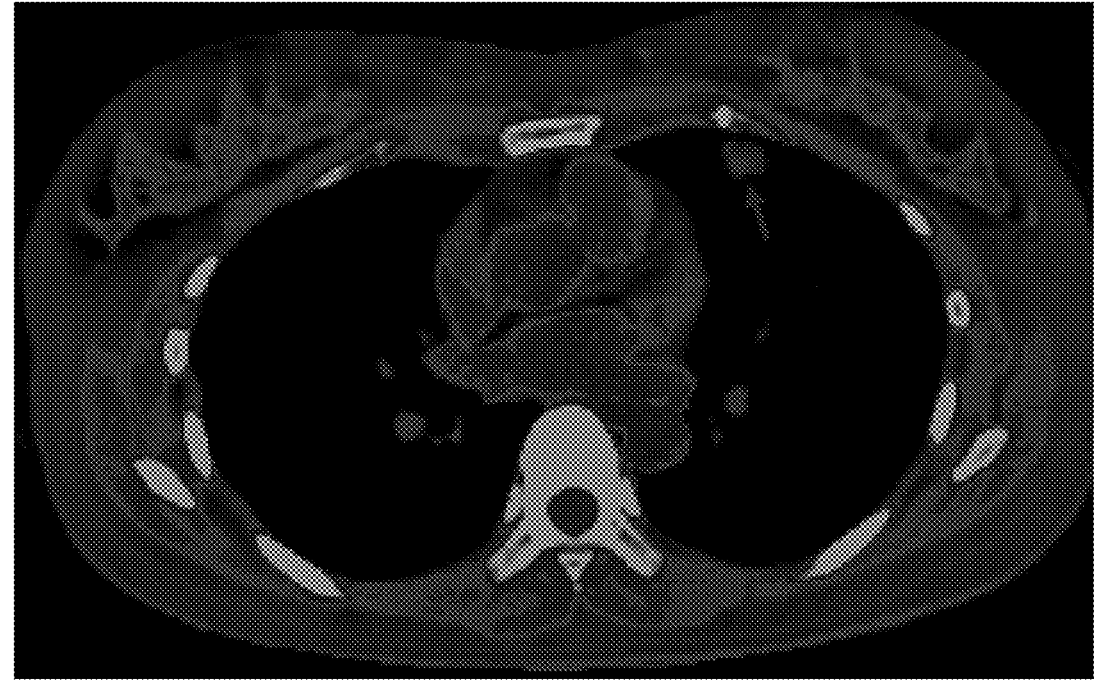
FIG. 4 is a schematic diagram of a color synthetic image of an embodiment of the present application.

For example, the third parameter value may be directly used as the pixel grayscale value to generate the synthetic image data and the synthetic image is a grayscale image. FIG. 3 is a schematic diagram of a grayscale synthetic image; or, the third parameter value may be used as the pixel grayscale value and then converted to a RGB value (mapping value) to generate the synthetic image data, then the synthetic image is a color image. FIG. 4 is a schematic diagram of a color synthetic image. For the method of converting the grayscale value to RGB value, the prior art may be referred to, which will not be repeated herein.

Figure 5A:
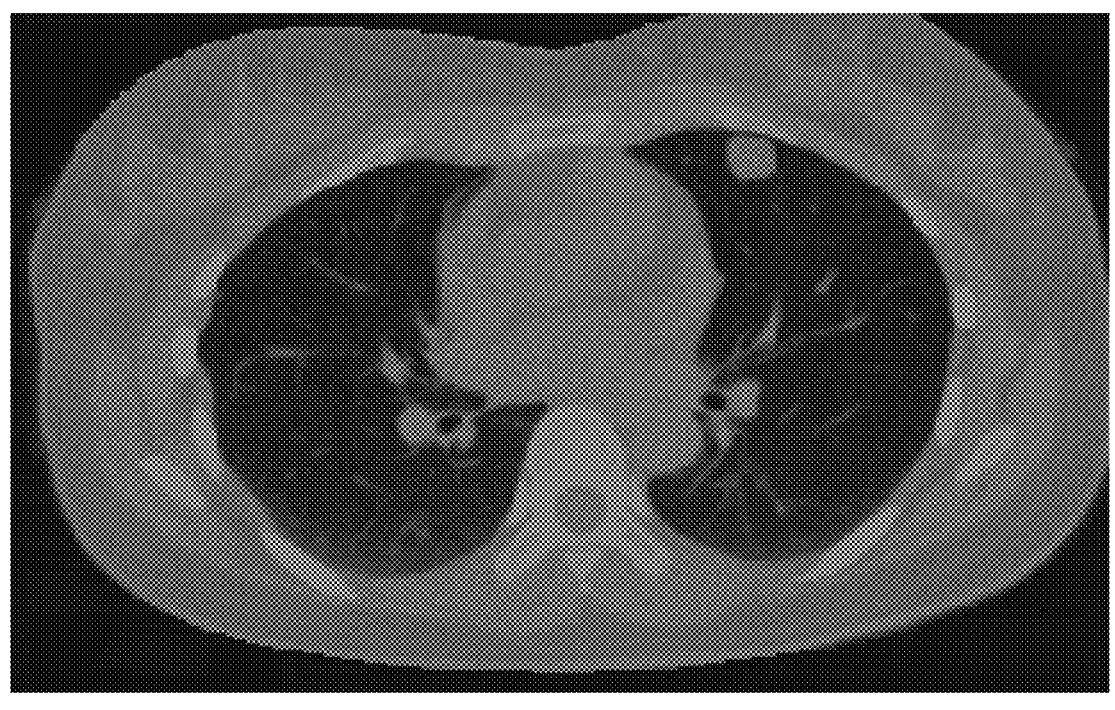
FIGS. 5A and 5B are schematic diagrams of a first medical image and a second medical image of an embodiment of the present application.
Figure 5B:
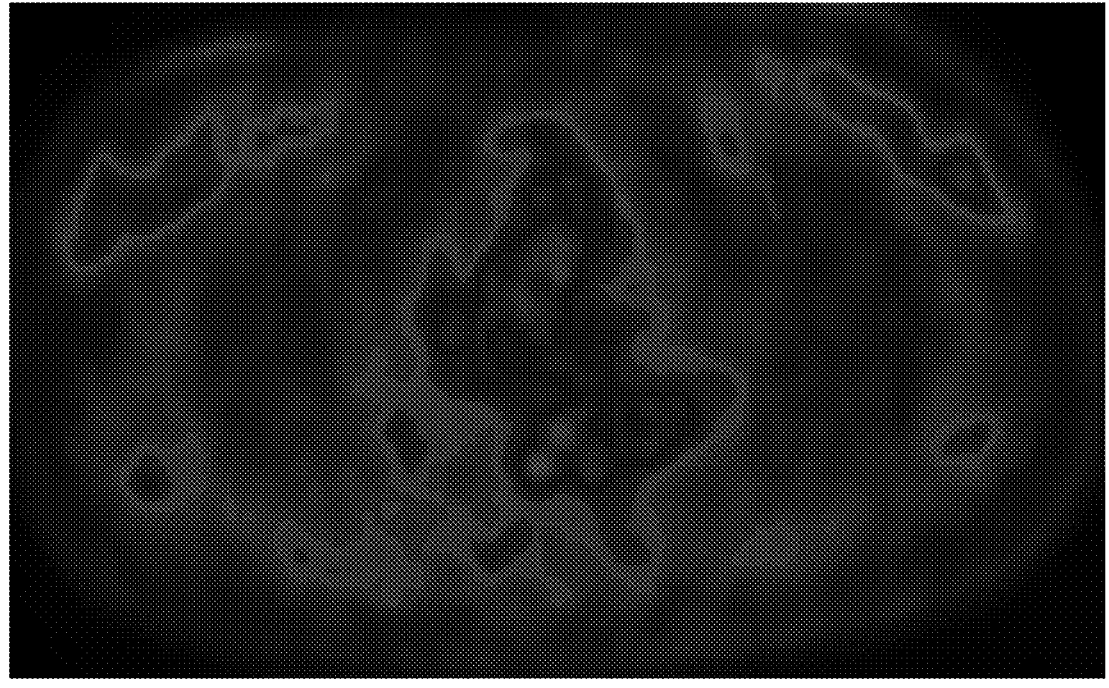
Figure 5C:
FIG. 5C is a schematic diagram of a synthetic image produced by a method in the prior art.

FIG. 5A is a schematic diagram of the first medical image in accordance with an embodiment. FIG. 5B is a schematic diagram of the second medical image. FIG. 5C is a schematic diagram of a conventional PET/CT fusion image in the prior art. As shown in FIG. 3 and FIG. 4, compared with FIG. 5A, FIG. 5B and FIG. 5C, the synthetic image has higher contrast and resolution, and the lesion region is clearer as shown by the arrow in the accompanied figure.

For example, the third image matrix may be converted to synthetic image data and the synthetic image data is stored in a predetermined data file type, which may be a DICOM file or NIFTI file as in the prior art, or may be a newly defined file type, and the embodiments of the present application are not limited thereto.

In some embodiments, where the first medical image is a CT image and the second medical image is a PET or SPECT image, the synthetic image is represented as SyPCT or SySPECT. The synthetic image may be used for quantitative analysis of tissue density and functional metabolism, enzymes or gene expressions as well as radiomics analysis.

It should be noted that the medical images described above in the embodiments of the present application are suitable for any region of interest of any scanned object, and the embodiments of the present application are not limited thereto.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

It is clear from the above embodiments that the first parameter value of the first medical image is multiplied with the second parameter value of the corresponding pixel location of the second medical image to generate a synthetic image based on the multiplication result. The multiplication of the first parameter value with the second parameter value is equivalent to an amplification of the difference between the pixel values at locations of the normal tissue and lesion tissue, resulting in a synthetic image with higher contrast and resolution, thus making the lesion region clearer and thereby improving the efficiency of lesion detection.

Embodiments of the present application provide a medical image synthesis device, and the same contents as in the embodiments of the first aspect are not repeated herein.

Figure 6:
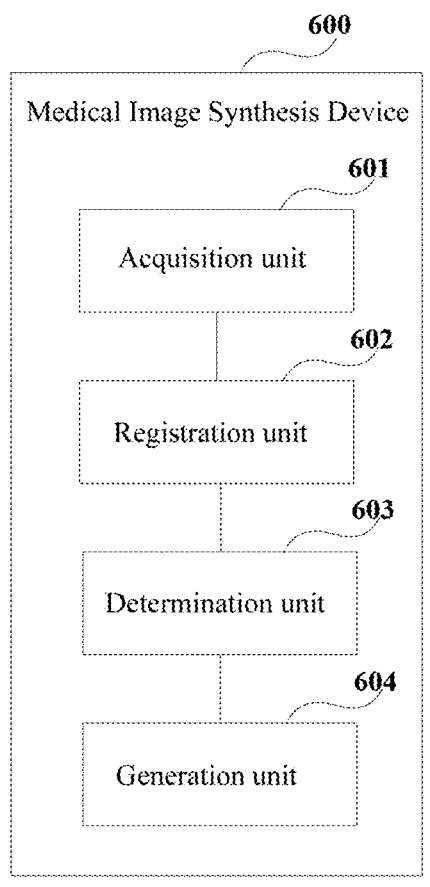
FIG. 6 is a schematic diagram of a medical image synthesis device of an embodiment of the present application.

FIG. 6 is a schematic diagram of a medical image synthesis device of an embodiment of the present application. As shown in FIG. 6, the medical image synthesis device 600 includes an acquisition unit 601, used to acquire a first medical image and a second medical image. The medical image synthesis device 600 includes a registration unit 602, used to register said first medical image with said second medical image. The medical image synthesis device 600 includes a determination unit 603, used to determine a first parameter value at each pixel location on the registered first medical image and a second parameter value at each pixel location on the second medical image. The medical image synthesis device 600 includes a generation unit 604, used to multiply the first parameter value with the second parameter value at the same pixel location on the registered first medical image and the second medical image, and generate synthetic image data based on the multiplication result.

In some embodiments, for the implementation of the acquisition unit 601, the registration unit 602, the determination unit 603, and the generation unit 604, reference may be made to 101-104 of the embodiments of the first aspect, which will not be repeated herein.

In some embodiments, said first medical image is an anatomical image and said second medical image is a molecular image.

In some embodiments, said first parameter value is a value corresponding to a linear attenuation coefficient of tissues or organs to rays of radiation and said second parameter value is a standardized uptake value.

In some embodiments, the device further includes a preprocessing unit used to carry out at least one of re-sampling, image enhancement or image denoising preprocessing procedures for said first medical image and said second medical image.

In some embodiments, the device further includes a correction unit used to correct said first parameter value and/or said second parameter value. And the generation unit 604 is configured to perform one of the following: multiply the first parameter value with the corrected second parameter value at the same pixel location on the registered first medical image and the second medical image; multiply the corrected first parameter value with the second parameter value at the same pixel location on the registered first medical image and the second medical image; or multiply the corrected first parameter value and the corrected second parameter value at the same pixel location on the registered first medical image and the second medical image.

In some embodiments, said generation unit 604 takes the multiplication result as the pixel value of the synthetic image corresponding to said same pixel location; or said generation unit 604 determines a mapping value corresponding to said multiplication result as the pixel value of the synthetic image corresponding to said same pixel location.

In some embodiments, the synthetic image is a grayscale image or a color image.

For the sake of simplicity, FIG. 6 only exemplarily illustrates a connection relationship or signal direction between various components or modules, but it should be clear to those skilled in the art that various related technologies such as bus connection can be used. The various components or modules can be implemented by means of a hardware facility such as a processor, a memory, etc. The embodiments of the present application are not limited thereto.

The above embodiments merely provide illustrative description of the embodiments of the present application. However, the present application is not limited thereto, and appropriate variations may be made on the basis of the above embodiments. For example, each of the above embodiments may be used independently, or one or more of the above embodiments may be combined.

It is clear from the above embodiments that the first parameter value of the first medical image is multiplied with the second parameter value of the corresponding pixel location of the second medical image to generate a synthetic image based on the multiplication result. The multiplication of the first parameter value with the second parameter value is equivalent to an amplification of the difference between the pixel values at locations of the normal tissue and lesion tissue, resulting in a synthetic image with higher contrast and resolution, thus making the lesion region clearer and thereby improving the efficiency of lesion detection.

Embodiments of the present application provide a medical image synthesis apparatus, comprising a medical image synthesis device 600 as described in the embodiments of the second aspect, and the contents of which are incorporated herein. The medical image synthesis apparatus may, for example, be a computer, a server, a workstation, a laptop, a smart phone, etc., but embodiments of the present application are not limited thereto.

Figure 7:
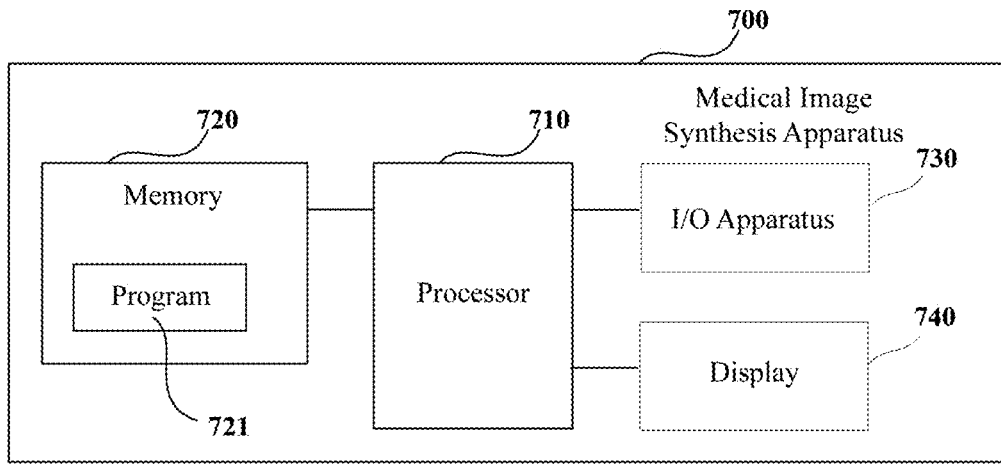
FIG. 7 is a schematic diagram of a medical image synthesis apparatus of an embodiment of the present application.

FIG. 7 is a schematic diagram of a medical image synthesis apparatus of an embodiment of the present application. As shown in FIG. 7, the medical image synthesis apparatus 700 may include: one or more processors (such as a central processing unit (CPU)) 710 and one or more memories 720 coupled to the processor 710. Wherein, the memory 720 can store various data and training models and the like. In addition, the memory 720 further stores a program 721 for information processing, and the program 721 is executed under control of the processor 710.

In some embodiments, functions of the medical image synthesis device 600 are integrated into and implemented by the processor 710. Wherein, the processor 710 is configured to implement the medical image synthesis method according to the embodiments of the first aspect.

In some embodiments, the medical image synthesis device 600 and the processor 710 are configured separately. For example, the medical image synthesis device 600 can be configured to be a chip connected to the processor 710 and the functions of the medical image synthesis device 600 can be achieved by means of the control of the processor 710.

For example, the processor 710 is configured to perform the following controls: acquiring a first medical image and a second medical image; registering the first medical image with the second medical image; determining a first parameter value at each pixel location on the registered first medical image and a second parameter value at each pixel location on the second medical image; and multiplying the first parameter value with the second parameter value at the same pixel location on the registered first medical image and the second medical image, and generating synthetic image data based on the multiplication result.

For example, the processor 710 is configured to perform the following controls: carrying out at least one of re-sampling, image enhancement or image denoising preprocessing procedures for said first medical image and said second medical image.

For example, the processor 710 is configured to perform the following controls: correcting the first parameter value and/or the second parameter value; and multiplying the first parameter value and the corrected second parameter value at the same pixel location on the registered first medical image and the second medical image; or multiplying the corrected first parameter value with the second parameter value at the same pixel location on the registered first medical image and the second medical image; or multiplying the corrected first parameter value and the corrected second parameter value at the same pixel location on the registered first medical image and the second medical image.

For example, the processor 710 is configured to perform the following controls: using the multiplication result as the pixel value at the same pixel location corresponding to the synthetic image; or, determining a mapping value corresponding to this multiplication result as the pixel value at the same pixel location corresponding to the synthetic image.

In some embodiments, for the implementation of processor 710, reference may be made to the embodiments of the first aspect, which will not be repeated herein.

In addition, as shown in FIG. 7, the medical image synthesis apparatus 700 may also include: an input-output (I/O) apparatus 730 and a display 740 (displaying a first medical image, a second medical image and a synthetic image), etc.; wherein the functions of the above components are similar to those of the prior art and will not be repeated herein. It should be noted that the medical image synthesis apparatus 700 does not necessarily include all of the components shown in FIG. 7. In addition, the medical image synthesis apparatus 700 may include components not shown in FIG. 7, for which the related art may be referred to.

It is clear from the above embodiments that the first parameter value of the first medical image is multiplied with the second parameter value of the corresponding pixel location of the second medical image to generate a synthetic image based on the multiplication result. The multiplication of the first parameter value with the second parameter value is equivalent to an amplification of the difference between the pixel values at locations of the normal tissue and lesion tissue, resulting in a synthetic image with higher contrast and resolution, thus making the lesion region clearer and thereby improving the efficiency of lesion detection.

Embodiments of the present application further provide a computer-readable program, wherein when the program is executed in a medical image synthesis apparatus, the program causes a computer to execute, in the medical image synthesis apparatus, the medical image synthesis method according to the embodiments of the first aspect.

Embodiments of the present application further provide a storage medium storing a computer-readable program, wherein the computer-readable program causes a computer to execute, in the medical image synthesis apparatus, the medical image synthesis method according to the embodiments of the first aspect.

The above device and method of the present application can be implemented by hardware, or can be implemented by hardware in combination with software. The present application relates to such a computer-readable program, when executed by a logical component, causes the logical component to implement the foregoing device or constituent part, or causes the logical component to implement various methods or steps as described above. The present application further relates to a storage medium for storing the above program, such as a hard disk, a magnetic disk, an optical disk, a DVD, a flash memory, etc.

The method/device described with reference to the embodiments of the present application may be directly embodied as hardware, a software module executed by a processor, or a combination of the two. For example, one or more of the functional block diagrams and/or one or more combinations of the functional block diagrams shown in the drawings may correspond to either respective software modules or respective hardware modules of a computer program flow. These software modules may respectively correspond to the steps shown in the figures. These hardware modules can be implemented, for example, by firming the software modules using a field-programmable gate array (FPGA).

The software modules may be located in a RAM, a flash memory, a ROM, an EPROM, an EEPROM, a register, a hard disk, a portable storage disk, a CD-ROM, or any storage medium in other forms known in the art. A storage medium may be coupled to a processor, so that the processor can read information from the storage medium and can write information into the storage medium. Alternatively, the storage medium may be a component of the processor. The processor and the storage medium may be located in an ASIC. The software module may be stored in a memory of a mobile terminal, and may also be stored in a memory card that can be inserted into a mobile terminal. For example, if an apparatus (such as a mobile terminal) uses a large-capacity MEGA-SIM card or a large-capacity flash memory device, the software modules can be stored in the MEGA-SIM card or the large-capacity flash memory device.

One or more of the functional blocks and/or one or more combinations of the functional blocks shown in the accompanying drawings may be implemented as a general-purpose processor, a digital signal processor (DSP), an application specific integrated circuit (ASIC), a field-programmable gate array (FPGA) or other programmable logic devices, discrete gate or transistor logic devices, a discrete hardware assembly, or any appropriate combination thereof for implementing the functions described in the present application. The one or more functional blocks and/or the one or more combinations of the functional blocks shown in the accompanying drawings may also be implemented as a combination of computing apparatuses, such as a combination of a DSP and a microprocessor, multiple microprocessors, one or more microprocessors in communication combination with a DSP, or any other such configuration.

One of the beneficial effects of the embodiments of the present application lies in that: a first parameter value of a first medical image is multiplied with a second parameter value of a second medical image at the corresponding pixel location to generate a synthetic image based on the multiplication result, and the multiplication of the first parameter value (e.g., the CT value of a CT image) and the second parameter value (e.g., the SUV of a PET image) is equivalent to an amplification of the difference between the pixel values at locations of the normal tissue and lesion tissue, resulting in a synthetic image with higher contrast and resolution, thus making the lesion region clearer and thereby improving the effectiveness of lesion detection.

The present application is described above with reference to specific implementations. However, it should be clear to those skilled in the art that such description is merely illustrative and is not intended to limit the scope of protection of the present application. Various variations and modifications could be made by those skilled in the art according to the principle of the present application, and these variations and modifications also fall within the scope of the present application.

What is claimed is:

1. A medical image synthesis device, comprising:
an acquisition unit used to acquire a first medical image and a second medical image;
a registration unit used to register said first medical image with said second medical image;
a determination unit used to determine a first parameter value at each pixel location on the registered first medical image and a second parameter value at each pixel location on the second medical image;
a correction unit configured to apply a first weighting coefficient to the first parameter value and a second weighting coefficient to the second parameter value to generate a to correct said first parameter value to generate a corrected first parameter value and to correct said second parameter value to generate a corrected second parameter value; and
a generation unit used to multiply, on a pixel by pixel basis, the corrected first parameter value with the corrected second parameter value at the same pixel location on the registered first medical image and the second medical image, and generate synthetic image data based on the multiplication result.

2. The medical image synthesis device according to claim 1, wherein said first medical image is an anatomical image and said second medical image is a molecular image.

3. The medical image synthesis device according to claim 1, wherein said first parameter value is a value corresponding to a linear attenuation coefficient of tissues or organs to rays of radiation and said second parameter value is a standardized uptake value.

4. The medical image synthesis device according to claim 1, further comprising: a preprocessing unit used to carry out at least one of re-sampling, image enhancement, or image denoising preprocessing procedures on said first medical image and said second medical image.

5. The medical image synthesis device according to claim 1,
wherein said generation unit multiplies the first parameter value with the corrected second parameter value at the same pixel location on the registered first medical image and the second medical image.

6. The medical image synthesis device according to claim 1,
wherein said generation unit multiplies the corrected first parameter value with the second parameter value at the same pixel location on the registered first medical image and the second medical image.

7. The medical image synthesis device according to claim 1, wherein said generation unit takes the multiplication result as the pixel value of a synthetic image corresponding to said same pixel location, or said generation unit determines a mapping value corresponding to said multiplication result as the pixel value of the synthetic image corresponding to said same pixel location.

8. The medical image synthesis device according to claim 1, wherein the image synthesized by said generation unit is a grayscale image or a color image.

9. The medical image synthesis device according to claim 1, wherein correcting said first parameter value to generate a corrected first parameter value includes using a first weighting coefficient and correcting said second parameter value to generate a corrected second parameter value includes using a second weighting coefficient.

10. The medical image synthesis device according to claim 1, wherein multiplying the first parameter value with the second parameter value at the same pixel location is equivalent to dot-multiplying the first image matrix and the second image matrix.

11. A method used for synthesizing a medical image, comprising:
acquiring a first medical image and a second medical image;
registering said first medical image with said second medical image;
determining a first parameter value at each pixel location on the registered first medical image and a second parameter value at each pixel location on the second medical image;
correcting said first parameter value by applying a first weighting coefficient to generate a corrected first parameter value and correcting said second parameter value by applying a second weighting coefficient to generate a corrected second parameter value; and
multiplying, on a pixel by pixel basis, the corrected first parameter value with the corrected second parameter value at the same pixel location on the registered first medical image and the second medical image, and generating synthetic image data based on the multiplication result.

12. The method of claim 11, wherein said first medical image is an anatomical image and said second medical image is a molecular image.

13. The method of claim 11, wherein said first parameter value is a value corresponding to a linear attenuation coefficient of tissues or organs to rays of radiation and said second parameter value is a standardized uptake value.

14. The method of claim 11, further comprising carrying out at least one of re-sampling, image enhancement or image denoising preprocessing procedures on said first medical image and said second medical image.

15. The method of claim 11, further comprising using a preprocessing unit to carry out at least one of re-sampling, image enhancement or image denoising preprocessing procedures on said first medical image and said second medical image.

16. A non-transitory storage medium having a computer-readable program stored thereon, wherein said computer-readable program causes a computer to perform the following steps:
acquiring a first medical image and a second medical image;
registering said first medical image with said second medical image;
determining a first parameter value at each pixel location on the registered first medical image and a second parameter value at each pixel location on the second medical image;
correcting said first parameter value by applying a first weighting coefficient to generate a corrected first parameter value and correcting said second parameter by applying a second weighting coefficient to generate a corrected second parameter value; and multiplying, on a pixel by pixel basis, the corrected first parameter value with the corrected second parameter value at the same pixel location on the registered first medical image and the second medical image, and generating synthetic image data based on the multiplication result.

17. The non-transitory storage medium of claim 16, wherein said first medical image is an anatomical image and said second medical image is a molecular image.

18. The non-transitory storage medium of claim 16, wherein said first parameter value is a value corresponding to a linear attenuation coefficient of tissues or organs to rays of radiation and said second parameter value is a standardized uptake value.

19. The non-transitory storage medium of claim 16, wherein the computer-readable program further causes the computer to perform at least one of re-sampling, image enhancement or image denoising preprocessing procedures on said first medical image and said second medical image.

\*   \*   \*   \*   \*